United States Patent [19]
Chang et al.

[11] Patent Number: 5,836,981
[45] Date of Patent: Nov. 17, 1998

[54] PACEMAKER CIRCUIT AND ASSOCIATED METHODS FOR GENERATING ELECTRICAL STIMULATION SIGNALS

[75] Inventors: Steve Chang, Valencia, Calif.; Robert R. Weyant, Redmond, Wash.

[73] Assignee: Paceseter, Inc., Sylmar, Calif.

[21] Appl. No.: 785,193

[22] Filed: Jan. 17, 1997

[51] Int. Cl.$^6$ .................................................. A61N 1/362
[52] U.S. Cl. ............................................................. 607/9
[58] Field of Search .................................. 607/5, 6, 7, 8, 607/9, 14

[56] References Cited

U.S. PATENT DOCUMENTS

5,366,485  11/1994  Kroll et al. ................................. 607/5
5,620,468   4/1997  Mongeon et al. .......................... 607/5

*Primary Examiner*—Scott M. Getzow

[57] ABSTRACT

A DC-to-DC converter circuit is disclosed for use in a pacemaker. The DC-to-DC converter circuit is capable of producing a pulse burst and boosting the voltage of the pulse burst up to an effective pacing amplitude, thereby eliminating the need for the multiple pump capacitors and the output capacitor. The DC-to-DC converter circuit uses a transformer to amplify the battery voltage to the required pacing amplitude. By using a transformer, DC leakage current is eliminated without the use of a decoupling capacitor, thereby achieving lower pacing thresholds. Also, each patient may be individually tested to determine their response to high frequency pulse bursts and a "customized" pacing waveshape can be produced by varying the duty cycle, polarity or pulse burst of each stimulation signal. The DC-to-DC converter circuit also reduces the polarization effect of the tissue around the electrodes.

26 Claims, 4 Drawing Sheets

PACEMAKER CIRCUIT AND ASSOCIATED METHODS FOR GENERATING ELECTRICAL STIMULATION SIGNALS

FIELD OF THE INVENTION

The present invention relates generally to cardiac pacemakers, and other types of implantable medical devices, which provide electrical stimulus to the heart to control the heart's rhythm. More particularly, the invention relates to circuits designed to generate pacing pulses.

BACKGROUND OF THE INVENTION

Cardiac pacing involves the electrical stimulation of the heart in order to control the timing of the contractions of the heart. Electrical stimuli in the form of pulses are generated by a battery-powered pacemaker and applied to the tissue of the heart by one or more electrodes that are connected to the pacemaker via flexible, insulated conductors. The insulated conductors and associated electrodes form what is referred to as the "lead."

The operation of a pacemaker as described above presupposes that the electrical stimulation generated by the pacemaker effectuates capture. As used herein, the term "capture" refers to the ability of a given stimulation signal generated by a pacemaker to cause depolarization of the myocardium, i.e., to cause the heart muscle to contract, or to cause the heart to "beat." The minimum amount of electrical stimulation that effectively evokes a cardiac contraction is commonly referred to as a patient's "capture threshold." Unfortunately, capture threshold varies significantly among patients; therefore, it is not desirable for the manufacturer to permanently set the amount of electrical stimulation provided by a pacemaker. Rather, it is preferable for stimulus parameters to be individually set for each patient immediately after implantation and during subsequent office visits.

Typically, a substantial safety margin is added to the measured capture threshold to ensure that the pacemaker continues to evoke contractions over an extended period of time. The safety margin is necessary because a patient's capture threshold varies over time; sometimes dramatically during the first few months following implantation. In some patients, the amplitude of the stimulation signal required by the safety margin is as high as 7.5 volts.

In current pacemakers, the output pulse is generated from the discharge of a capacitor through the pacing leads. The output capacitor is charged from the battery at a relatively slow rate to the programmed output voltage. Since the battery voltage of lithium-iodine cells (the type of battery commonly used within pacemakers) is approximately 2.8 volts, delivery of a stimulus of greater amplitude requires the use of a voltage multiplier. The typical voltage multiplier involves the use of several "pump" capacitors that in turn are used to charge a larger output capacitor. For example, the output voltage may be doubled by charging two pump capacitors in parallel, and then connecting the pump capacitors in series to charge the output capacitor. This technique will be described in greater detail below.

Many pulse generators used today for permanent cardiac pacing deliver a capacitively coupled pulse of programmable duration. When the fully charged output capacitor is discharged, the resulting voltage at the leading edge of the pulse is independent of the pacing impedance (the impedance of the insulated conductors combined with the natural impedance of the body). However, the trailing edge of the pulse is usually somewhat less in voltage than that of the leading edge, with the voltage difference being a function of the pacing impedance. Specifically, because the output capacitor stores a charge of a fixed quantity, the greater the current flow, the smaller the charge remaining on the capacitor at the end of the pulse (producing a lower voltage at the end of the pulse). One consequence of this decay in the pulse amplitude is that a higher initial voltage may be required to achieve a state of capture than would be needed in the absence of such decay.

In addition to effectuating capture, the delivery of a stimulation signal has several negative effects. First, when a pacemaker delivers the stimulation signal, the ions around the stimulating electrode are polarized. This polarization results in a residual charge remaining in the vicinity of the pacing electrodes after each application of a signal. The quantity of the residual charge is directly proportional to both the signal amplitude and the signal duration. If the residual charge in dual-chamber pacing systems is of sufficient quantity in the atrium, the charge may erroneously be sensed by the sensing amplifier in the ventricle (known as crosstalk), resulting in the inhibition in the output of a stimulation pulse by the pacemaker. Because of this potential for inhibition of pacing due to crosstalk, the ventricular sensing circuit is typically deactivated for a period of time (the blanking period) following the delivery of an atrial pacing stimulus. Despite these precautionary measures, the residual charge is usually large enough so that crosstalk remains a potential clinical problem with unipolar pacing and sensing.

A second negative effect of the stimulation signal is to deplete the life of the pacemaker battery. The useable life of a pacemaker is normally limited by the life of the pacemaker battery. The battery life is greatly influenced by, among other factors, the current drain of the integrated circuitry, the amplitude and duration of the stimulation signal, the frequency of stimulation, and the total impedance of the pacing lead. Among these factors, the major source of current drain for the present generation of pacemakers is the stimulation signal. Thus, the amplitude, duration, and frequency of the stimulation signals are major contributors to the life of the power source.

What is needed is a pulse generator for use in a pacemaker that is able to deliver an effective stimulation signal without the need for the bulky pump and output capacitors. The pulse generator should minimize the amount of energy needed to deliver the stimulation signal and decrease the polarization effect around the electrodes. Additionally, the pulse generator should be isolated from the heart to eliminate the need for an output decoupling capacitor.

SUMMARY OF THE INVENTION

The present invention comprises a DC-to-DC converter circuit capable of generating a pacing signal for delivery to a patient. Recent developments in battery technology have made possible the use of lithium-monoflouride (Li-CFx) batteries in pacemakers. Li-CFx batteries provide significantly higher current capabilities than the current lithium-iodine batteries (i.e. 10 mA for Li-CFx vs. 100 $\mu$A for Li-I) in widespread use in today's pacemakers. As a result, with the DC-to-DC converter circuit, a pacing signal can be delivered directly from the battery without the use of a large output capacitor. The DC-to-DC converter circuit of the present invention also provides the ability to deliver a pacing signal to the heart while boosting the battery voltage up to an effective pacing amplitude, thereby eliminating the need for the multiple pump capacitors and the output capacitor commonly used in existing pacemakers. Because the pump capacitors and output capacitors tend to be large, bulky components, elimination of these capacitors saves valuable space in the pacemaker. In addition, because these large capacitors tend to be energy-inefficient, the replacement of the capacitor based charge pump circuit with the DC-to-DC converter circuit of the present invention conserves battery power and thereby extends the life of the implanted device.

In accordance with another aspect of the present invention, the DC-to-DC converter circuit may optionally be used to convert each stimulation signal into a corresponding pulse burst. By delivering a pulse burst in place of the conventional stimulation pulse, the DC-to-DC converter provides an even further savings of battery energy (as much as 50% if the pulse burst duty cycle is 0.5 for a constant amplitude and pulse width) for each stimulation signal. This energy saving results in less battery use and consequently an overall longer service life of the pacemaker. As used herein, a "pulse burst" is a rapid sequence of pulses used to cause a single contraction event. The "stimulation signal" is the signal required to cause a single contraction event of the heart, whether as a single pulse or a rapid sequence (or "burst") of pulses. The "pacing signal" refers to the overall signal provided by the pacemaker, usually a string of stimulation signals.

In the preferred embodiment, the DC-to-DC converter circuit uses a transformer to amplify the battery voltage to the required pacing amplitude. By using a transformer, DC leakage current is eliminated without the use of a de-coupling capacitor. Without the de-coupling capacitor, a true square wave stimulation signal can be delivered to the heart without the exponential decay normally associated with resistor-capacitor based circuits. By eliminating the exponential decay, the present invention is capable of achieving lower pacing thresholds. Also, with the use of programmable control circuitry which is coupled to the DC-to-DC converter, each patient may be individually tested to determine his or her response to the high frequency pulse bursts and a "customized" pacing waveshape can be produced by varying the pulse frequency, duty cycle, and polarity of the pulse burst within each stimulation signal.

The DC-to-DC converter circuit of the present invention also reduces the polarization effect of the tissue around the electrodes. As describe above, stimulation signals tend to polarize the tissue surrounding the electrodes, with the strength of the residual charge being directly related to the amplitude and duration of the stimulation signal. By delivering a high frequency pulse burst, the net amplitude and duration of the stimulation signal is reduced, producing a corresponding reduction in the strength of the residual charge. By reducing the residual charge, the present invention enhances the sensing capability of the pacemaker and reduces crosstalk.

BRIEF DESCRIPTION OF THE DRAWINGS

These and other features of the invention will now be described with reference to the drawings of certain preferred embodiments, which are intended to illustrate and not limit the invention, and in which.

DETAILED DESCRIPTION OF THE PREFERRED EMBODIMENT

Figure 1:
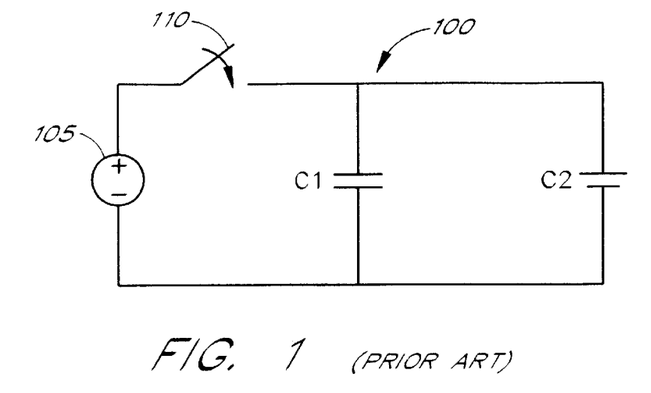
FIG. 1 is a high-level schematic diagram of a pacemaker voltage doubler charging circuit.
Figure 2:
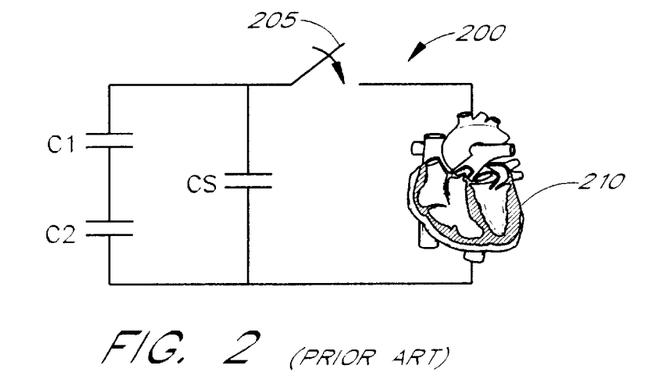
FIG. 2 is a schematic diagram of a pulse delivery circuit which makes use of components of the charging circuit of FIG. 1.

A typical capacitor based charging and delivery circuit as used in prior art pacemakers is shown in FIGS. 1 and 2. FIG. 1 shows a charging circuit 100 as used in prior art pacemakers to transfer electrical charge from a lithium-iodine battery 105 to a set of pump capacitors C1 and C2 connected in parallel. Once the capacitors C1 and C2 have been charged, they are reconfigured within the circuit so they are connected in series to deliver their charge to a storage capacitor CS, as illustrated in FIG. 2.

The charging circuit of FIG. 1 comprises the battery 105, a switch 110, and the pump capacitors C1 and C2. A first terminal of the battery is connected to a first terminal of the switch. The second terminal of the switch is connected to a first terminal of the capacitor C1 and to a first terminal of the capacitor C2. The second terminal of the capacitor C1 is connected to the second terminal of the capacitor C2 and to the second terminal of the battery 105.

In operation, the charging circuit 100 charges the two pump capacitors C1 and C2, thereby obtaining a two-times multiplication of the battery voltage when the capacitors are subsequently connected in series. However, it can be appreciated that additional capacitors may be added in parallel to increase the multiplication of the battery voltage. To charge the pump capacitors C1 and C2, the switch 110 closes allowing the battery 105 to charge the pump capacitors C1 and C2 to the full battery 105 voltage. When the pump capacitors C1 and C2 are charged to the full battery 105 voltage, the switch 110 opens.

FIG. 2 shows a pacing circuit 200 used in the prior art to deliver a pacing signal to a human heart 210 after the pump capacitors C1 and C2 have been charged. The pacing circuit comprises the charged pump capacitors C1 and C2, a storage capacitor CS, and a switch 205, and is coupled to the heart 210 by a conventional lead system (not shown). The storage capacitor CS is connected in parallel with the series combination of the pump capacitors C1 and C2. The circuit formed by the capacitors is coupled to the heart by the switch 205 and the lead system.

In operation, the pump capacitors C1 and C2 are initially connected in series so that the voltage across each capacitor C1 and C2 is added to charge the storage capacitor CS to a voltage equal to the sum of the voltages across the capacitors C1 and C2. After the storage capacitor CS is fully charged, a pacing voltage is applied to the heart 210 by (programmable) closing the switch 205. With the switch 205 closed, the storage capacitor CS discharges (partially) through the switch 205 to stimulate the heart 210. After the storage capacitor CS is discharged, the pump capacitors C1 and C2 are reconfigured into the charging circuit 100 of FIG. 1 to begin a new charging cycle. This recharge/delivery cycle is repeated with each stimulation signal that is applied to the heart. As stated above, the pump capacitors C1 and C2 and storage capacitor CS tend to be large, bulky components. Elimination of these capacitors saves valuable space in the pacemaker. In addition, because the capacitors C1, C2 and CS tend to be energy-inefficient, the replacement of the capacitor based charge pump circuit with the DC-to-DC converter circuit of the present invention conserves battery power and thereby extends the life of the implanted device.

Figure 3:
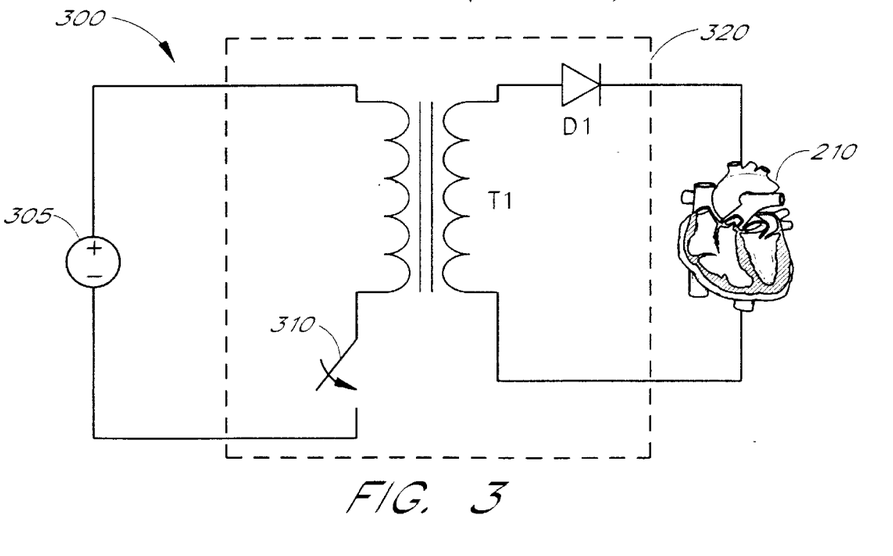
FIG. 3 is a high level schematic diagram of a DC-to-DC converter circuit in accordance with a preferred embodiment of the present invention.

FIG. 3 is a schematic representation of the DC-to-DC converter circuit 300 in accordance with the present invention. The DC-to-DC converter circuit 300 comprises a lithium-monoflouride (Li-CFx) or similar battery 305, and a signal generation and delivery stage 320. The signal generation and delivery stage 320 comprises a switch 310, a step-up transformer T1 and a diode D1. A first terminal of the Li-CFx battery 305 is connected to a first terminal on the primary side of the transformer T1. A second terminal on the primary side of the transformer T1 is connected to a first terminal of the switch 310. A second terminal of the switch 310 is connected to a second terminal of the battery 305. A first terminal on the secondary side of the transformer T1 is connected to the anode of the diode D1. The cathode of the diode D1 is connected to the first attachment to the heart 210. The second attachment to the heart 210 is connected to a second terminal on the secondary side of the transformer. In operation, the switch 310 controls the frequency and duty cycle of the signal applied to the transformer T1. The transformer T1 is a step-up transformer with the turns ratio dependant upon the amplification desired. The amplified signal received on the secondary side of the transformer T1 is sent through the diode D1 via standard lead systems (not shown) to the heart 210. Because the transformer T1 provides isolation between the battery 305 and the heart 210, the DC leakage current associated with charge pump circuits is eliminated without the need for an output de-coupling capacitor. This eliminates the exponential decay on the envelope of the pulse waveform. Elimination of the exponential decay results in lower pacing thresholds, as will be discussed in more detail below.

Figure 4:
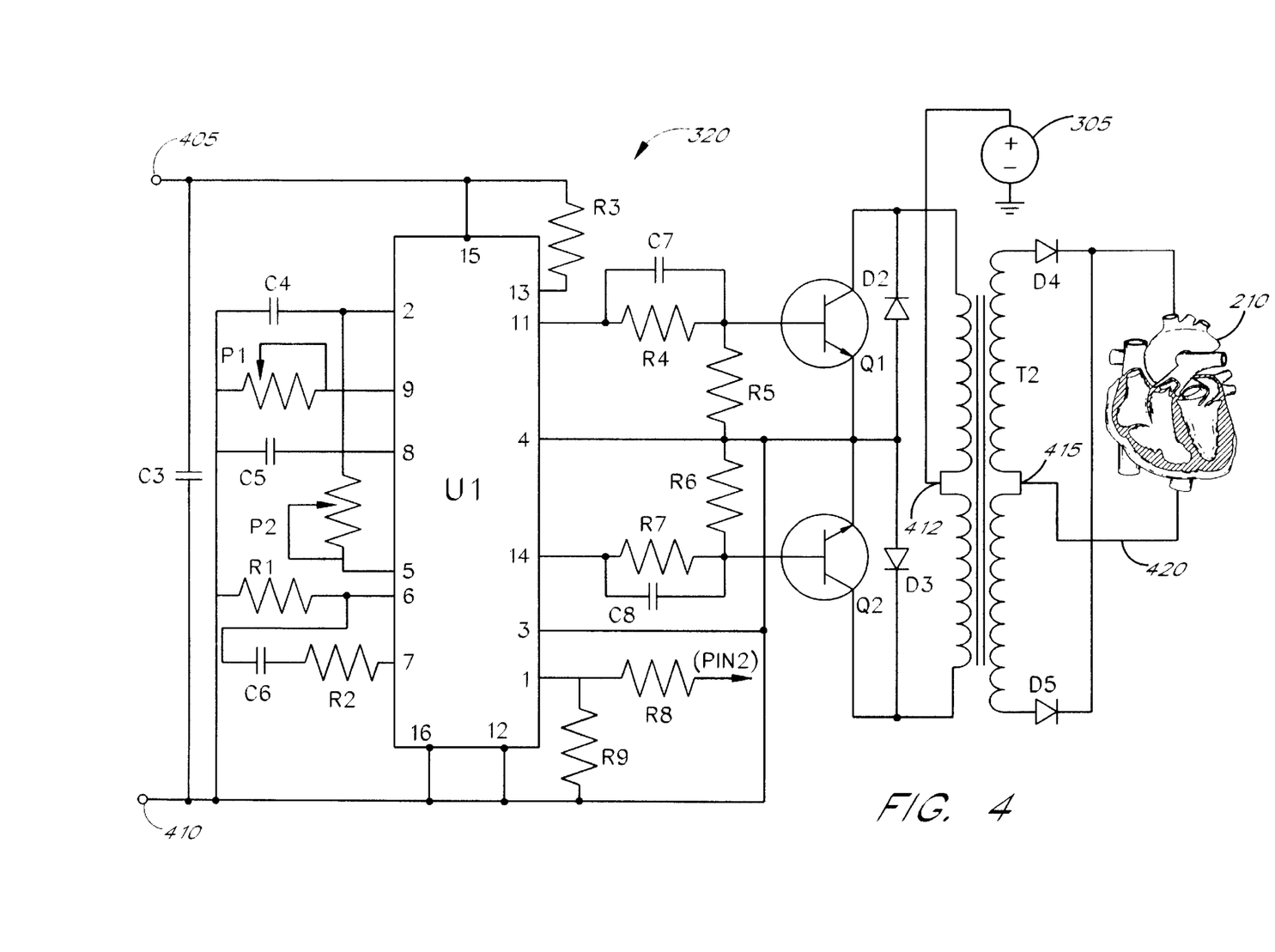
FIG. 4 is a circuit diagram illustrating the switching circuit of FIG. 3 in greater detail.

One embodiment of the signal generation and delivery stage 320 used to generate waveforms with a variety of frequencies and duty cycles is shown in FIG. 4. (The term "frequency" is used herein to refer to the rate at which individual pulses are generated within each pulse burst.) In this embodiment, the signal generation and delivery stage 320 comprises a controller U1, six capacitors C3–C8, nine resistors R1–R9, two potentiometers P1 and P2, two transistors Q1 and Q2, a transformer T2 and four diodes D2–D5. A first terminal of the capacitor C3 is connected to a positive voltage rail 405, to the supply voltage ($V_{IN}$) pin 15 of the controller U1, and to a first terminal of the resistor R3. A second terminal of the capacitor C3 is connected to a negative voltage rail 410, to a first terminal of the capacitor C4, to a first terminal of the potentiometer P1, to a first terminal of the capacitor C5, to a first terminal of the resistor R1, to the shutdown pin 16, the ground pin 12, the negative current sense pin 3 and the positive current sense pin 4 of the controller U1, and to a first terminal of the resistor R9. A second terminal of the capacitor C4 is connected to the reference ($V_{REF}$) pin 2 of the controller U1 and to a first terminal of the potentiometer P2. A second terminal of the potentiometer P1 is connected to the oscillator charging current ($R_T$) pin 9 of the controller U1. A second terminal of the capacitor C5 is connected to the oscillator capacitor input ($C_T$) pin 8, of the controller U1. A second terminal of the potentiometer P2 is connected to the positive error amp pin 5 of the controller U1. A second terminal of the resistor R1 is connected to a first terminal of the capacitor C6 and to the negative error amp pin 6 of the controller U1. A second terminal of the capacitor C6 is connected to a first terminal of the resistor R2. A second terminal of the resistor R2 is connected to the compensation pin 7 of the controller U1. A second terminal of the resistor R3 is connected to the collector supply voltage ($V_C$) pin 13 of the controller U1. A second terminal of the resistor R9 is connected to a first terminal of the resistor R8 and to the current limit pin 1 of the controller U1. A second terminal of the resistor R8 is connected to $V_{REF}$, pin 2 of the controller U1. A first output pin 11 of the controller U1 is connected to a first terminal of the capacitor C7 and to a first terminal of the resistor R4. The positive current sense pin 4 of the controller U1 is connected to a first terminal of the resistor R5, to a first terminal of the resistor R6, to the negative current sense pin 3 of the controller U1, to the negative voltage rail 410, to the emitter of the transistor Q1, to the emitter of the transistor Q2, to the anode of the diode D2, and to the anode of the diode D3. A second output pin 14 of the controller U1 is connected to a first terminal of the resistor R7 and to a first terminal of the capacitor C8. The sync pin 10 of the controller U1 is not used.

A second terminal of the capacitor C7 is connected to a second terminal of the resistor R4, to a second terminal of the resistor R5, and to the base of the transistor Q1. A second terminal of the capacitor C8 is connected to a second terminal of the resistor R7, to a second terminal of the resistor R6, and to the base of the transistor Q2. The collector of the transistor Q1 is connected to the cathode of the diode D2 and to a first terminal on the primary side of the transformer T2. The collector of the transistor Q2 is connected to the cathode of the diode D3 and to a second terminal on the primary side of the transformer T2. The first terminal of the Li-CFx battery 305 is connected to a tap in the primary side of the transformer T2. The second terminal of the Li-CFx battery 305 is connected to ground.

A first terminal on the secondary side of the transformer T2 is connected to the anode of the diode D4. The cathode of the diode D4 is connected to the first attachment to the heart 210 and to the cathode of the diode D5. The anode of the diode D5 is connected to a second terminal on the secondary side of the transformer T2. A tap on the secondary side of the transformer T2 is connected to the floating circuit ground 420, which is connected to the second attachment to the heart 210.

The signal generation and delivery stage 320 receives a signal from the positive voltage rail 405 and supplies the signal to pin 15, the supply voltage ($V_{IN}$) of the controller U1 to power the controller U1. The voltage at the positive voltage rail 405 is dropped across the resistor R3 and the remaining voltage is supplied to pin 13, $V_C$ of the controller U1.

The controller U1 outputs complementary signals on the first output pin 11 and the second output pin 14. The duty cycle and frequency of these signals may be varied by the controller U1. The combination of the inputs to the oscillator capacitor input pin 8 and the oscillator charging current pin 9 control the frequency of an internal oscillator circuit of the controller U1. The details of the internal oscillator circuit of the controller U1 are available from the Unitrode controller data sheets for the Current Mode PWM Controller which are incorporated herein by reference. When the controller is first activated, the frequency of the output signals at pins 11 and 14 is set by the relationship between the inputs to pin 9 and pin 8. By adjusting the value of the potentiometer P1, the input to pin 9 of the controller U1 is changed. The input to pin 8 remains unchanged. This alters the relationship between pin 8 and pin 9, and as a result adjusts the frequency of the signals at the output pins 11 and 14.

The duty cycle of the output signals at pins 11 and 14 may also be adjusted by the controller U1. The value of the input at the positive error amp pin 5 controls the duty cycle of the controller U1. By adjusting the value of the potentiometer P2, the current input at the error amp pin 5 is changed thereby varying the relationship between pin 5 and the reference voltage pin 2. Changing this relationship adjusts the duty cycle of the output signal at pins 11 and 14. In the preferred embodiment, duty cycles from 0 to 100 percent may be obtained.

The output signals at pins 11 and 14 are used to drive the transistors Q1 and Q2. The transistors Q1 and Q2 are arranged in a push-pull configuration. When an output signal is present at the first output pin 11, the voltage delivered to the base of the transistor Q1 turns on the transistor Q1. When the transistor Q1 is on, current is allowed to flow from the Li-CFx battery 305 and into the center tap 412 on the primary side of the transformer T2. The current passes through the transformer, into the collector of the transistor Q1, out of the emitter of the transistor Q1, and to the negative voltage rail 410. The current flowing through the primary side of the transformer T2 causes current flow in the secondary side of the transformer T2. The current flows out of the transformer T2, through the diode D4 to be delivered to the heart 210. The heart 210 and the center tap 415 on the secondary side of the transformer T2 are connected to form a floating ground to complete the circuit path.

When an output signal is present at the second output pin 14, the voltage delivered to the base of the transistor Q2 turns on the transistor Q2. When the transistor Q2 is on, current is allowed to flow from the Li-CFx battery 305 and into the center tap 412 on the primary side of the transformer T2. The current passes through the transformer, into the collector of the transistor Q2, out of the emitter of the transformer Q2, and to the negative voltage rail 410. The current flowing through the primary side of the transformer T2 causes current flow in the secondary side of the transformer T2. The current flows out of the transformer T2, through the diode D5 to be delivered to the heart 210. The heart 210 and the center tap 415 on the secondary side of the transformer T2 are connected to form a floating ground to complete the circuit path.

Figure 5:
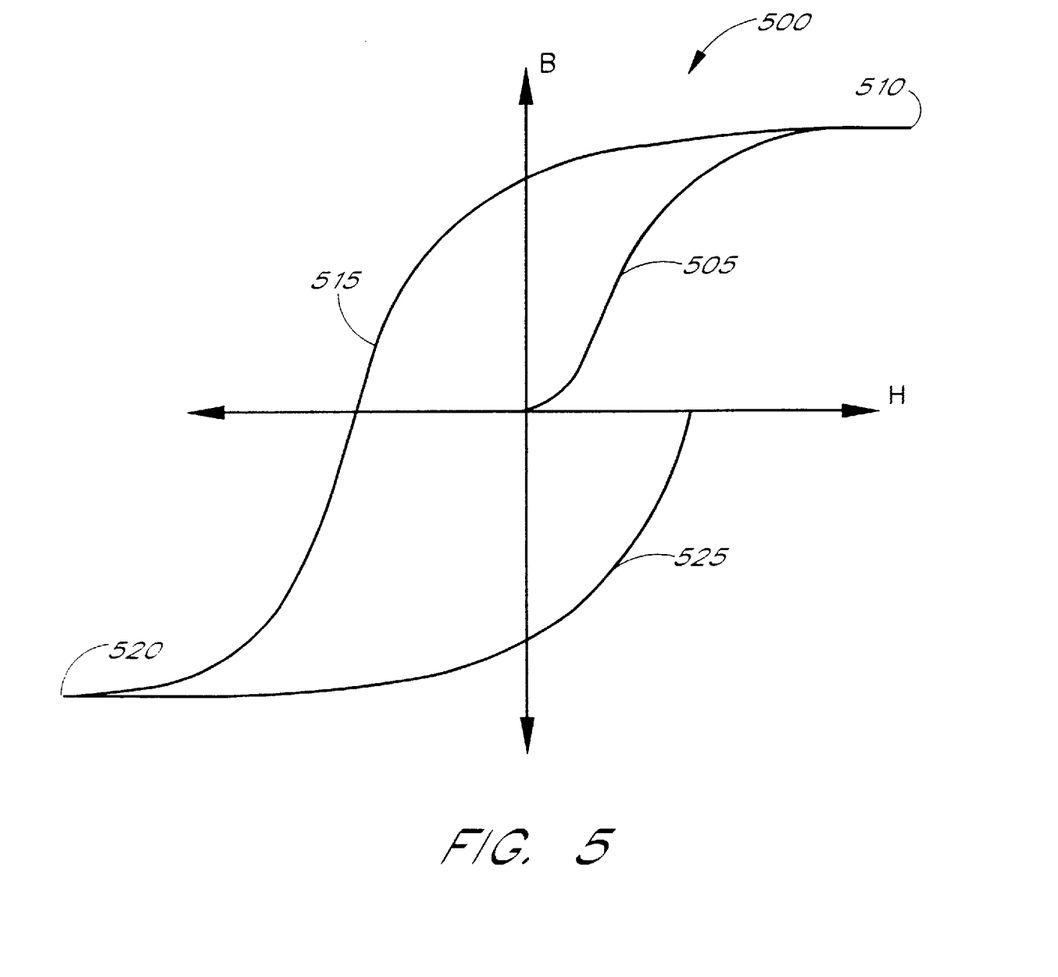
FIG. 5 is a diagram illustrating the general shape of the B-H curve of the transformer in FIG. 4.

The combination of the transistors Q1 and Q2 are used to minimize the size of the transformer T2 necessary to achieve a proper step-up voltage. Because the transistors Q1 and Q2 are arranged in a push-pull topology, the current sent through the transformer T2 will vary the magnetic state of the transformer T2. This can be seen by examining the magnetic B-H curve 500 of the transformer T2 as seen generally in FIG. 5. When the transistor Q1 is on, the transformer T2 receives a positive magnetic charge and travels along a charging path 505 of the B-H curve 500. As the transformer T2 approaches a positive magnetic peak 510, the transformer T2 approaches saturation. One common technique to prevent saturation is to use a larger transformer, which expands the size of the B-H curve 500. However, in the pacemaker field, the size of all components is critical and should be kept to a minimum. Therefore, to enable the use of a small transformer T2, the push-pull topology of the transistors Q1 and Q2 is used to prevent transformer saturation. As the transformer T2 approaches the positive magnetic peak 510, the transistor Q1 turns off and the transistor Q2 turns on, thereby reversing current flow through the transformer T2. As a result, the magnetic state of the transformer T2 travels along a second charging path 515 of the B-H curve 500 toward a negative magnetic peak 520. As the magnetic state of the transformer T2 approaches the negative magnetic peak 520, the transistor Q2 turns off and the transistor Q1 turns on, again reversing current flow through the transformer T2. The magnetism of the transformer T2 then travels along another charging path 525 of the B-H curve 500. The transistors Q1 and Q2 repetitively cycle on and off to reverse the current flow through the transformer T2, thereby preventing saturation. This allows a smaller transformer to be used to obtain the proper step-up of the voltage.

Of course, it is generally desirable to minimize the size of the pacemaker. As a result, the above circuitry including the functionality of the controller U1 are preferably incorporated into microcircuitry for implantation into a pacemaker. It will also be appreciated that the circuitry described herein is merely representative of a preferred technique for implementing the DC-to-DC converter circuit. For example, the duty cycle and frequency adjustment of the output signals is preferably accomplished via software or firmware under control of a microprocessor, rather than by varying the settings of potentiometers. Techniques for incorporating devices of the type described herein into microcircuitry are well known in the art and will not be described herein.

In the preferred embodiment, the capacitor C3 is a 1 $\mu$F capacitor, the capacitor C4 is a 0.1 $\mu$F capacitor, the capacitor C5 is a 0.005 $\mu$F capacitor, the capacitor C6 is a 0.0015 $\mu$F capacitor, and the capacitors C7 and C8 are 0.05 $\mu$F capacitors. The resistor R1 is a 3.2 K$\Omega$ resistor, the resistor R2 is a 64 K$\Omega$ resistor, the resistor R3 is a 200$\Omega$ resistor, the resistors R4 and R7 are 10$\Omega$ resistors, the resistors R5, R6 and R9 are 1000$\Omega$ resistors, and the resistor R8 is a 1500$\Omega$ resistor. The potentiometer P1 adjusts to a maximum of 500 ohms and the potentiometer P2 adjusts to a maximum of 3.2 Kohms. The transistors Q1 and Q2 are 2N2222 transistors and the diodes D2–D5 are 14942 diodes. The controller U1 is a UC3846 manufactured by Unitrode Integrated Circuits Corporation of Merrimack, N.H. The transformer is a P0704 potcore transformer and the turn ratio is dependant upon the amount of voltage amplification required (which in turn depends upon the type of battery used). For example, if three times the battery voltage is desired, a transformer with a turn ratio of 1:3 may be used.

Figure 6A:
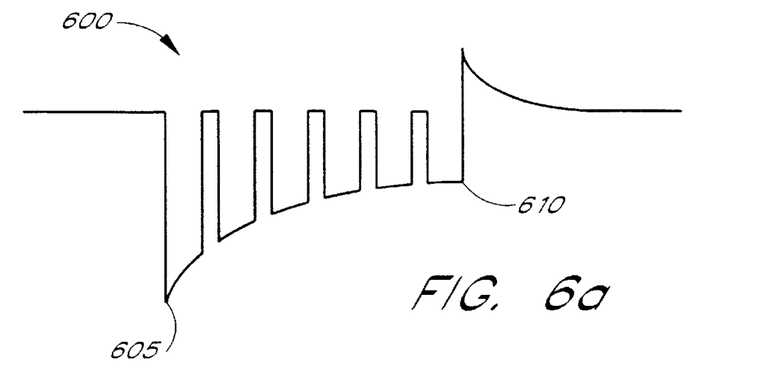
FIG. 6a is a representative output waveform obtained from the circuit of FIG. 3 with the use of a coupling capacitor.
Figure 6B:
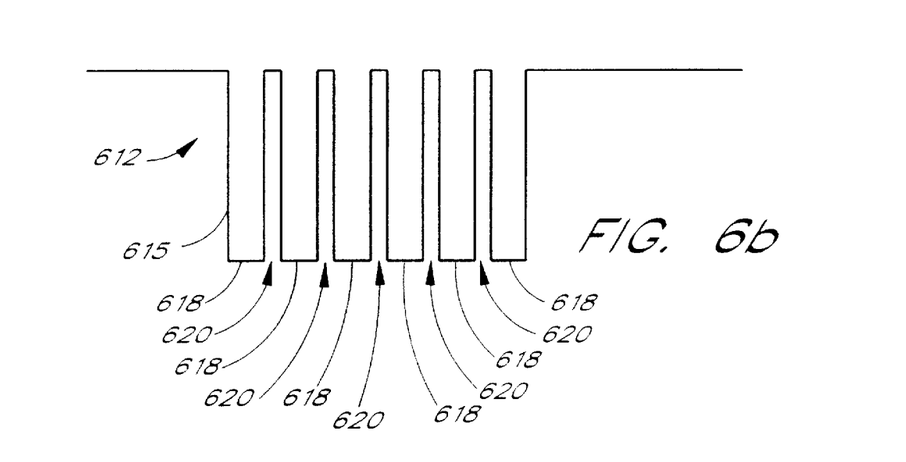
FIG. 6b is a representative output waveform obtained from the circuit of FIG. 3 without a coupling capacitor.
Figure 6C:
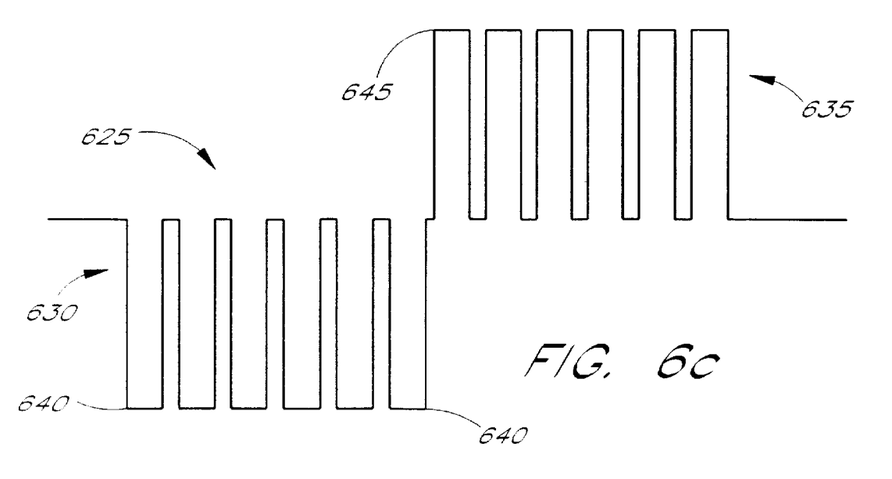
FIG. 6c is a representative biphasic waveform that may be produced using the circuit in FIG. 3.

The DC-to-DC converter circuit of FIG. 3 is capable of producing a variety of output signals (in the form of pulse bursts) as seen in FIGS. 6a–6c. FIG. 6a is provided as a reference waveform 600 produced when a de-coupling capacitor is used in combination with the DC-to-DC converter circuit of FIG. 3. In this embodiment, the DC-to-DC converter circuit provides a square wave output with a peak voltage 605. Due to the effect of the decoupling capacitor, the output waveform 600 decays exponentially from the peak voltage 605 to an end voltage 610. As a result, the average voltage delivered to the heart over the life of the waveform has a value between the peak voltage 605 and the end voltage 610. This creates an inefficiency in the pacemaker circuitry. For example, if the capture threshold (the minimum voltage necessary to achieve capture) is 3 volts, the peak voltage 605 of the waveform 600 may need to be 4–5 volts to ensure the average voltage of the waveform is 3 volts. The battery delivers the 4–5 volts over the entire life of the waveform but the decoupling capacitor in combination with the impedance of the pacing leads causes the voltage decay. This results in the battery delivering a higher amount of energy than is necessary to effectively pace the heart, resulting in a shorter battery life.

Because the DC-to-DC converter circuit of the present invention uses a transformer to isolate the battery from the heart, the need for a decoupling capacitor is eliminated. In addition to the savings in space resulting from removing the decoupling capacitor, a significant amount of energy is also saved.

FIG. 6b shows a square wave pulse burst 612 produced by the circuit of FIG. 3. The square wave pulse burst has a peak voltage 615. Because the decoupling capacitor is removed from the circuit, the peak voltage 615 does not experience the exponential decay seen in the waveform 600. Consequently, the peak voltage 615 is the average voltage delivered to the heart. This allows the battery to more closely provide the amount of energy required to achieve capture, resulting in an extended battery life. Also, because the pulse burst 612 has a duty cycle below 100 percent, the pulse burst 612 is divided in powered sections 618 and non-powered sections 620. No energy is required from the battery during the non-powered sections 620 of the pulse burst 612. As a result, a pulse burst 612 of peak voltage 615 is delivered to the heart using less power than is needed for a steady-state (non-pulsed) DC voltage of the same amplitude and duration, thereby extending battery life. Additionally, the use of a pulse burst 612 as seen in FIG. 6b decreases the polarization effect of the heart. As described above, the tissue around the electrodes polarizes whenever a signal is delivered to the heart. By using the pulse burst 612, a signal is only delivered to the heart during the powered sections 618 of the pulse burst 612. Therefore, the tissue in the heart does not polarize during the non-powered sections 620 of the pulse burst 612. This results in significantly less polarization of the heart tissue during the entire waveform, and therefore reduces the amount of crosstalk received by the sensors.

The duty cycle and frequency of the pulse burst 612 may be adjusted programmably as necessary. Because the DC-to-DC converter circuit of the present invention allows for frequency and duty cycle adjustment, an individual patient may be tested (either interactively using a pacemaker programmer or automatically using program routines) to determine his most efficient output waveform. Some patients may be able to accept a lower duty cycle waveform and still capture the heart. More energy can be saved by lowering the duty cycle of the output waveform.

With the addition of a well-known "H bridge" circuitry to the DC-to-DC converter of the present invention, a biphasic pulse burst 625 output can be obtained as shown in FIG. 6c. The biphasic pulse burst 625 has a negative voltage portion 630 and a positive voltage portion 635. It may be possible to achieve capture with a lower peak voltage 640 by using the biphasic pulse burst 625. When the biphasic pulse burst 625 changes polarity, the heart sees a voltage equal to the difference between the negative peak 640 and a positive peak 645. Because the DC-to-DC converter circuit can provide both positive and negative voltages, and some patients may experience a lower threshold voltage with a biphasic pulse burst 625, additional potential for energy savings exists. Of course, the biphasic pulse burst 625 may still exploit all the other advantages of the DC-to-DC converter circuit, including variable duty cycle and the absence of the decoupling capacitor.

Numerous variations and modifications of the invention will become readily apparent to those skilled in the art. Accordingly, the invention may be embodied in other specific forms without departing from its spirit or essential characteristics. The detailed embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. An implantable stimulation device having a pacing circuit for providing a stimulation signal to a heart, comprising:
    a battery which provides a DC voltage signal;
    a switching stage which receives the DC voltage signal and generates a pulse burst having a first voltage, the pulse burst being defined as a rapid sequence of pulses used to cause a single contraction event; and
    a transformer which boosts the first voltage of the pulse burst to generate the stimulation signal having a second voltage suitable for capturing the heart.

2. The implantable stimulation device of claim 1, wherein the frequency and duty cycle of the pulse burst is adjustable.

3. The implantable stimulation device of claim 1, wherein the transformer isolates the battery from the heart thereby eliminating the need for an output decoupling capacitor.

4. The implantable stimulation device of claim 1, wherein the voltage of the stimulation signal remains constant.

5. The implantable stimulation device of claim 1, wherein the battery is a lithium-monoflouride battery.

6. The implantable stimulation device of claim 1, wherein the switching stage comprises:
    a controller which generates a first output signal and a second output signal, wherein the frequency and duty cycle of the first and second output signals are adjustable by the controller;
    a first transistor activated by the first output signal, wherein the first transistor directs current a first direction through the transformer; and
    a second transistor activated by the second output signal, wherein the second transistor directs current a second direction through the transformer, wherein the second direction is electrically opposite of the first direction and thereby prevents the transformer from magnetically saturating.

7. The implantable stimulation device of claim 1, further comprising control circuitry for adjusting the voltage of the pulse burst to correspond to a capture threshold of the heart.

8. The implantable stimulation device of claim 1, wherein at least two of the pulses of the sequence are of opposite polarity.

9. A pacemaker signal generator which converts energy from a battery to provide a pacing signal to a heart, the signal generator comprising:
    a controller which generates a first output signal and a second output signal;
    a transformer which multiplies the voltage from the battery to create a stimulation signal of sufficient voltage to achieve capture of the heart; and
    a switching stage which receives the first and second output signals from the controller, wherein the switching stage determines the direction of current flow through the transformer based upon the values of the first and second output signals.

10. The pacemaker signal generator of claim 9, wherein the voltage of the stimulation signal remains constant.

11. The pacemaker signal generator of claim 9, wherein the stimulation signal comprises a pulse burst, wherein the pulse burst is a rapid sequence of pulses.

12. The pacemaker signal generator of claim 11, wherein at least two of the pulses of the pulse burst are of opposite polarity.

13. A method of providing a stimulation signal to a heart, the method comprising the steps of:

receiving a DC input signal;

generating a pulse burst from the DC input signal, the pulse burst being defined as a rapid sequence of pulses used to cause a single contraction event;

isolating the heart from the DC input signal; and boosting a voltage of the pulse burst to create the stimulation signal.

14. The method of claim 13, wherein a plurality of the stimulation signals comprise a pacing signal.

15. The method of claim 13, further comprising the step of adjusting the duty cycle of the pulse burst.

16. The method of claim 13, further comprising the step of adjusting the frequency of the pulse burst.

17. The method of claim 13, wherein the isolation step is accomplished using a transformer.

18. An implantable stimulation device having a pacing circuit for generating a pacing signal for application to a heart, comprising:

means for providing a DC voltage;

means for converting the DC voltage to a pulse burst having a first voltage, the pulse burst being defined as a rapid sequence of pulses used to cause a single contraction event; and means for boosting the first voltage of the pulse burst to create the pacing signal having a second voltage suitable for application to the heart.

19. A method of stimulating the contraction of a human heart so as to conserve battery power, comprising:

providing a battery-powered, implantable stimulation device which uses a lead to apply electrical pacing signals to the myocardium of the heart;

generating a stimulation signal within the implantable stimulation device, the stimulation signal comprising a sequence of voltage pulses of like polarity; and applying the stimulation signal to the myocardium via the lead in order to generate a single contraction of a chamber of the heart.

20. The method of claim 19, wherein the stimulation signal comprises a sequence of pulses of substantially equal amplitude.

21. The method of claim 19, wherein the stimulation signal comprises a sequence of pulses of substantially equal duration.

22. The method of claim 19, wherein the pulses of the sequence are equally spaced apart in time.

23. The method of claim 19, wherein at least two of the pulses of the sequence are of opposite polarity.

24. The method of claim 19, wherein the step of generating comprises applying a non-amplified sequence of voltage pulses to a winding of a step-up transformer.

25. The method of claim 19, further comprising adjusting an amplitude of the sequence of pulses to correspond to a capture threshold of the patient.

26. An implantable cardiac stimulation device, comprising:

voltage means for providing a first voltage;

sensing means for sensing cardiac activity;

pulse generating means for generating a pacing stimulation signal in the absence of any cardiac signals, the pulse generating means including means for generating a pulse burst as the stimulation signal, the pulse burst being defined as a rapid sequence of pulses spaced in such a way as to cause a single contraction event and having sufficient energy to capture a patient's heart.

* * * * *